(12) United States Patent
Kobayashi et al.

(10) Patent No.: US 8,758,361 B2
(45) Date of Patent: Jun. 24, 2014

(54) INSERTION DEVICE FOR INTRAOCULAR LENS

(75) Inventors: Kenichi Kobayashi, Urayasu (JP); Kimiya Shimizu, Tokyo (JP)

(73) Assignee: Staar Japan, Inc., Urayasu-shi, Chiba (JP)

( * ) Notice: Subject to any disclaimer, the term of this patent is extended or adjusted under 35 U.S.C. 154(b) by 1276 days.

(21) Appl. No.: 11/612,813

(22) Filed: Dec. 19, 2006

(65) Prior Publication Data
US 2008/0027460 A1    Jan. 31, 2008

(30) Foreign Application Priority Data

Dec. 20, 2005  (JP) ................................. 2005-367171
Jul. 27, 2006  (JP) ................................. 2006-205397

(51) Int. Cl.
*A61F 9/00*    (2006.01)

(52) U.S. Cl.
USPC .......................... 606/107; 623/6.12; 623/6.13

(58) Field of Classification Search
USPC ................... 623/6.12, 6.13; 606/107
See application file for complete search history.

(56) References Cited

U.S. PATENT DOCUMENTS

| | | | |
|---|---|---|---|
| 4,634,423 A * | 1/1987 | Bailey, Jr. ..................... | 606/198 |
| 4,699,140 A | 10/1987 | Holmes et al. | |
| 6,179,843 B1 | 1/2001 | Weiler | |
| 2002/0055776 A1 * | 5/2002 | Juan et al. .................... | 623/6.12 |
| 2004/0267359 A1 * | 12/2004 | Makker et al. ............... | 623/6.12 |

FOREIGN PATENT DOCUMENTS

| | | |
|---|---|---|
| EP | 1 481 652 A1 | 12/2004 |
| JP | 2003-325568 | 11/2003 |
| JP | 2004-261263 | 9/2004 |
| JP | 2004-351196 | 12/2004 |
| WO | 2004/112893 | 12/2004 |

* cited by examiner

*Primary Examiner* — Victor Nguyen
*Assistant Examiner* — Kevin Everage
(74) *Attorney, Agent, or Firm* — John K. Fitzgerald; Fulwider Patton LLP

(57) ABSTRACT

An insertion device is disclosed which is suitable for use of liquid as lubricant such as normal saline. The insertion device for inserting a lens into an eye comprises a main body having a nozzle at its front end, and a pushing member for pushing the lens set in the main body into an eye through the nozzle. The pushing member includes an introducing portion through which liquid is introduced and a flow path for supplying the liquid introduced from the introducing portion into the main body.

10 Claims, 9 Drawing Sheets

INSERTION DEVICE FOR INTRAOCULAR LENS

BACKGROUND OF THE INVENTION

1. Field of the Invention

The present invention relates to an insertion device for inserting into an eye an intraocular lens which is inserted instead of a crystal lens after the crystal lens is extracted because of cataract or inserted into an eye in order to cure abnormal refraction.

2. Description of the Related Art

In the case of a surgery for cataract, the central portion of the anterior capsule of an eyeball is ablated, a clouded crystal lens is removed by an ultrasonic suction apparatus, and then an artificial intraocular lens is placed to the position of the removed clouded crystal lens. When placing the lens in the eyeball, a surgery method for inserting the lens into the eyeball through a small incision by using the flexibility of the lens and thereby deforming the lens into a small shape, e.g. folding the lens is the mainstream. Thereby, astigma after surgery is prevented.

Then, in the case of a surgery, an insertion device is frequently used which deforms the lens into a small shape while moving the lens set in the main body of the insertion device by a pushing shaft and pushes the lens into an eye from the front opening of an insertion cylinder (nozzle) inserted into the incision. This insertion device is used not only for the surgery of cataract but also for a lens inserting surgery for a vision correction treatment.

When the lens is inserted into an eye by using the insertion device, a viscoelastic material such as hyaluronate sodium is introduced into the insertion device as a lubricant so that the lens is smoothly moved and deformed in the insertion device. Moreover, the viscoelastic material has a function of spreading the space of the anterior chamber of the eye into which the lens will be inserted.

Conventionally, a viscoelastic material is introduced from the front opening of the insertion cylinder by using a syringe or introduced from the introducing port provided on the main body of the insertion device (see Japanese Patent Laid-Open No. 2004-351196).

However, when using a viscoelastic material, the following problems occur.

1. The viscoelastic material that entered an eye together with a lens requires difficulty or labor hours to remove the material from the eye due to its viscosity. Therefore, the time required for the surgery is increased.

2. Since a space into which a lens is inserted in an eye is small, when the viscoelastic material enters the eye before the lens, the space is blocked by the viscoelastic material and it is difficult to insert the lens into the space.

3. Most viscoelastic materials including hyaluronate sodium are expensive.

Thus, the viscoelastic material is effective as lubricant, but it also has disadvantages. Therefore, it is requested to use low-viscosity inexpensive normal saline which is generally used for surgeries in place of the viscoelastic material.

BRIEF SUMMARY OF THE INVENTION

The present invention provides an insertion device suitable for use of liquid as lubricant such as normal saline.

The present invention in its first aspect provides an insertion device for inserting a lens into an eye, which comprises a main body having a nozzle at its front end, and a pushing member for pushing the lens set in the main body into an eye through the nozzle. The pushing member includes an introducing portion through which liquid is introduced and a flow path for supplying the liquid introduced from the introducing portion into the main body.

The present invention in its second aspect provides an insertion device for inserting a lens into an eye, which comprises a main body having a nozzle at its front end, and a pushing member for pushing the lens set in the main body into an eye through the nozzle. A flow path for ejecting liquid from the inside of the main body is formed within the thickness of the peripheral wall of the nozzle.

The present invention in its third aspect provides an insertion device for inserting a lens into an eye, which comprises a main body having a nozzle at its front end, and a pushing member for pushing the lens set in the main body into an eye through the nozzle. A groove serving as a flow path for ejecting liquid from the inside of the main body is formed on the inner face of the peripheral wall of the nozzle.

The present invention in its fourth aspect provides an insertion device for inserting a lens into an eye, which comprises a main body having a nozzle at its front end, and a pushing member for pushing the lens set in the main body into an eye through the nozzle. An opening for ejecting liquid from the inside of the main body is formed on the peripheral wall of the nozzle.

Other objects and features of the present invention will become readily apparent from the following description of the preferred embodiments with reference to accompanying drawings.

DETAILED DESCRIPTION OF THE PREFERRED EMBODIMENTS

Preferred embodiments of the present invention are described below by referring to the accompanying drawings.

Embodiment 1

Figure 1:
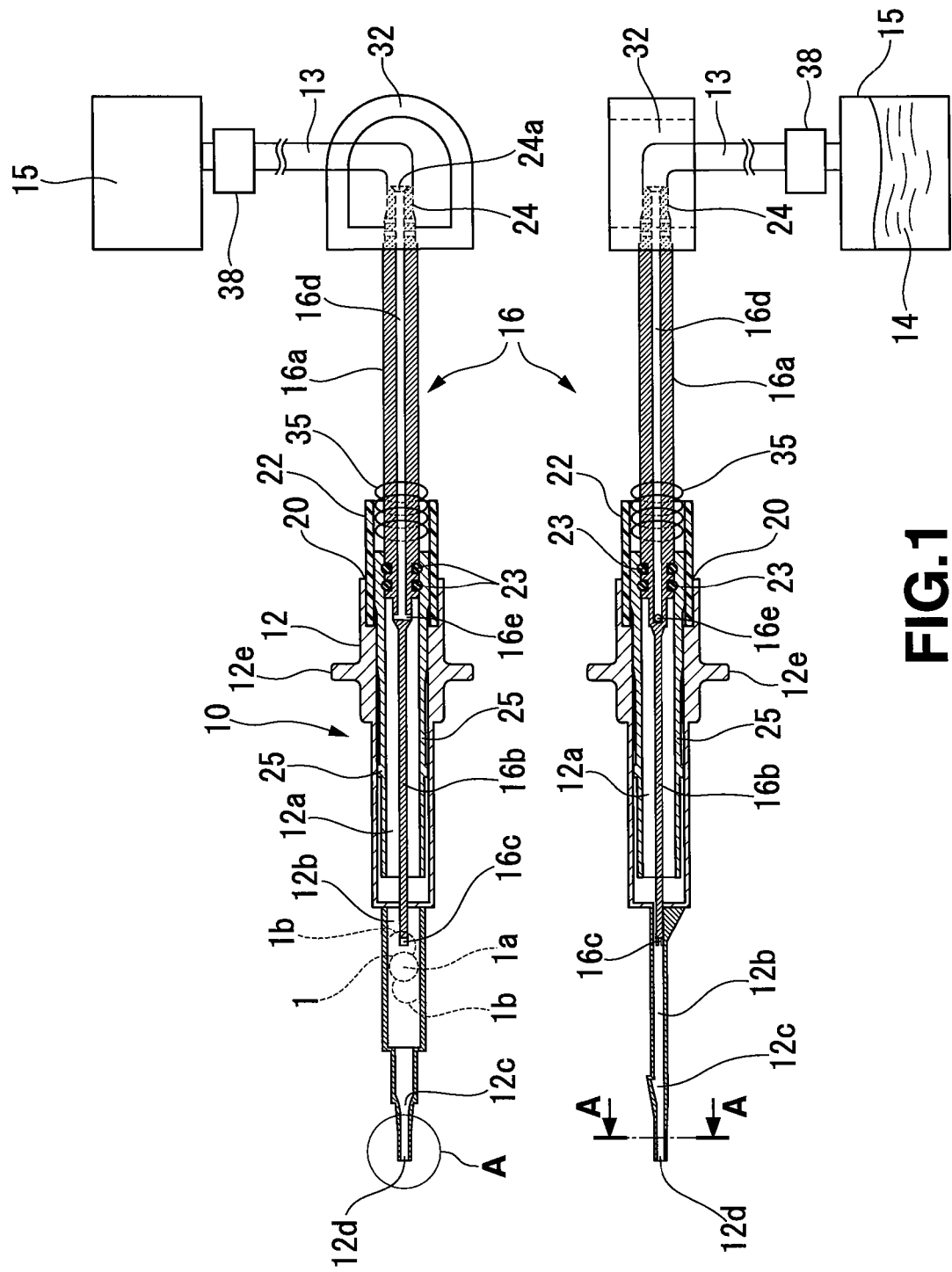
FIG. 1 is a side view and a top view showing an intraocular lens inserting system which is Embodiment 1 of the present invention.
Figure 2:
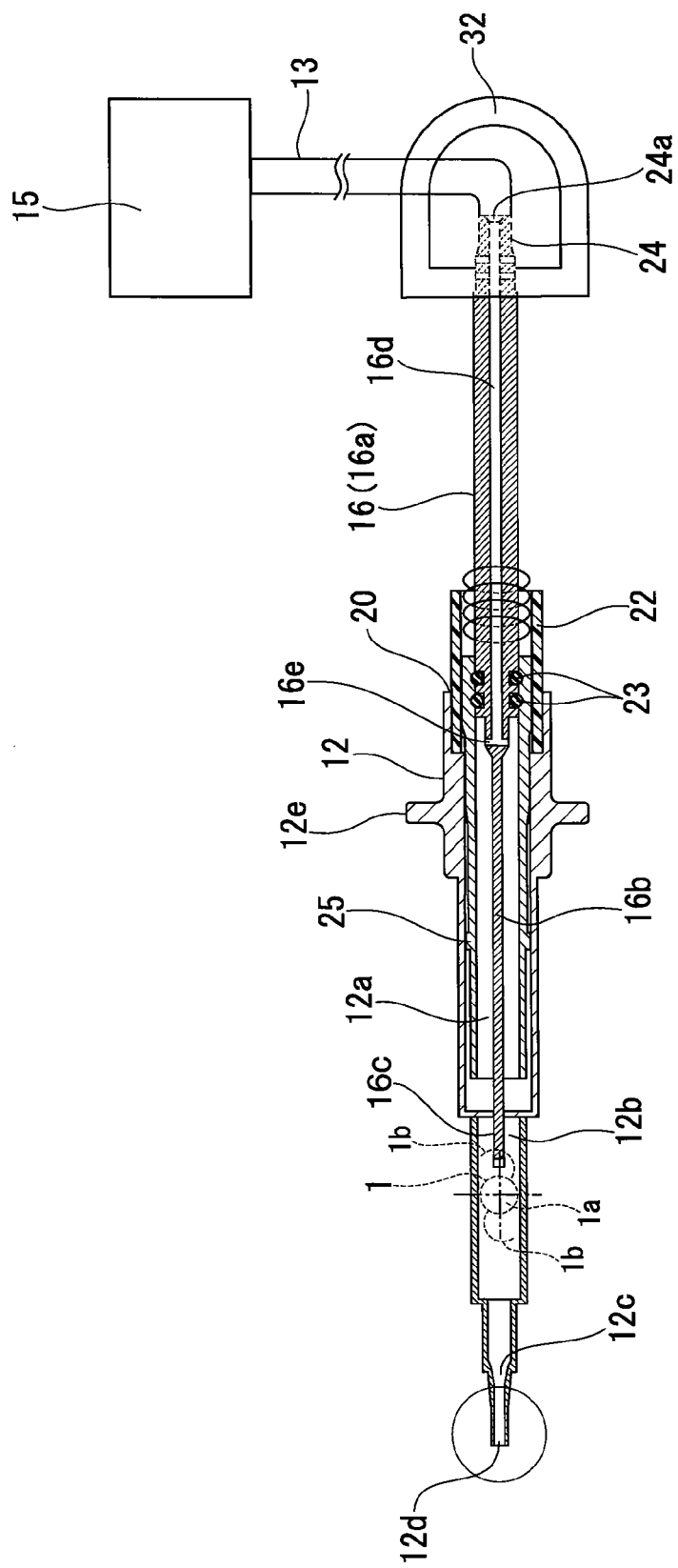
FIG. 2 is an upside sectional view of FIG. 1, which is an illustration showing a flow path by hatching it.

FIG. 1 shows an intraocular lens inserting system which is Embodiment 1 of the present invention. The upperside in FIG. 1 shows a top view thereof and the lowerside shows a side view thereof. FIG. 2 is a section view of the inserting system.

Reference numeral 10 denotes the insertion device for an intraocular lens of this embodiment (hereinafter referred to as a lens) and 15 denotes a feeder for feeding liquid 14 such as normal saline to the insertion device 10.

The insertion device 10 is constituted of a main body 12 and pushing shaft (pushing member) 16. The main body 12 is formed as an integral component having a cylindrical portion 12a, a lens holding portion 12b provided at the front end of the cylindrical portion 12a, a nozzle portion 12c provided at the front end of the lens holding portion 12b, and a hand-held portion 12e provided at the rear end (opposite to the nozzle portion 12c) of the cylindrical portion 12a. The cylindrical portion 12a and hand-held portion 12e respectively have a hollow structure and the pushing shaft 16 is inserted into the hollow structure.

The lens holding portion 12b has a hollow flat plate shape and a lens 1 is housed and held in the lens holding portion 12b in a state in which a stress is not substantially applied to an optical portion (portion substituted for crystal lens in an eye) 1a of the lens 1. The state in which a stress is not substantially applied denotes a state in which a stress or a deformation influencing the optical function of the optical portion 1a does not occur even if the lens 1 is stored for a long time. The lens 1 includes the optical portion 1a 1 and supporting portions 1b which support the optical portion 1a in the eye and are formed of a wire rod or the like. To make it possible to set the lens 1 to the lens holding portion 12b, the lens holding portion 12b has a configuration in which the portion 12b is vertically divided into two portions or a lid of the portion 12b is opened or closed.

The configuration of the lens 1 is not limited to the above case. It is allowed that the configuration has an optical portion and a flat-plate supporting portion. Moreover, in this embodiment, a so-called preload-type insertion device is described in which the lens 1 is previously set to the lens holding portion 12b before it is delivered to a hospital such as the time when it is shipped from a plant. However, it is possible to apply the present invention to an insertion device other than the above one. For example, the present invention can be applied to an insertion system in which an insertion device and a lens are separately stored and the lens is set to the insertion device immediately before a surgery.

Moreover, in this embodiment, a case of including the main body 12 in which the hand-held portion 12e to nozzle portion 12c are integrally formed is described. However, an insertion device of the present invention is not limited to the above case. For example, the present invention can be applied to an insertion device in which a nozzle portion is attached to a main body that a hand-held portion to a lens holding portion are integrally formed. Moreover, the present invention can be applied to an insertion device in which a component having a nozzle portion and a lens holding portion is attached to a main body having a cylindrical portion and a hand-held portion. These insertion devices are included in the present invention because the integrated part from the hand-held portion to the nozzle portion functions as a main body after it is assembled (at the time of use).

The pushing shaft 16 has a first shaft portion 16a exposed from the main body 12 before inserting the lens 1 into the eye and a second shaft portion 16b provided at the front end of the first shaft portion 16a and extending in the axis direction in the main body 12. A lens contact portion 16c which contacts the lens 1 held by the lens holding portion 12b and pushes the lens 1 into the eye through the nozzle portion 12c when inserting the lens 1 into the eye is formed at the front end of the second shaft portion 16b.

An introducing portion 24 is formed at the rear end of the pushing shaft 16 (first shaft portion 16a). A tube 13 extending from the feeder 15 is connected to the introducing portion 24.

An introducing opening 24a for introducing normal saline from the tube 13 is formed at the inside of the introducing portion 24. Moreover, a flow path 16d extending in the front end direction (axis direction) from an introducing opening 24a is formed in the first shaft portion 16a. The front end of the flow path 16d is opened to a space in the main body 12 at the front end of the first shaft portion 16a, in other words, a portion (intermediate portion) closer to the rear-end portion than the lens contact portion 16c of the pushing shaft 16. The opening serves as a flow-out opening 16e through which the normal saline enters the main body 12.

As the feeder 15, an apparatus may be used which feeds the liquid 14 to the insertion device 10 by putting the liquid 14 in a bottle and using the pressure difference generated by making the liquid level higher than the insertion device 10. Moreover, it is allowed to use the irrigation portion of an ultrasonic emulsification suction apparatus generally used for cataract surgery as the feeder 15.

In the insertion system thus constituted, when the liquid 14 such as normal saline is fed from the feeder 15 to the introducing portion 24 (introducing opening 24a) of the insertion device 10, the liquid 14 passes through the flow path 16d in the pushing shaft 16 and flows into the inner space of the hand-held portion 12e of the main body 12 from the flow-out opening 16e. Then, the liquid 14 passes through the inner space of the cylindrical portion 12a and flows to the lens holding portion 12b and further the nozzle portion 12c and is ejected to the outside from the front end opening 12d of the nozzle portion 12c.

FIG. 2 shows the flow path of the liquid 14 extending from the feeder 15 to the front-end opening 12d of the nozzle portion 12c by hatching it. Properly setting the flow rate of the liquid 14 from the feeder 15 makes it possible to always flow the liquid 14 in the direction of the nozzle portion 12c in the main body 12 and cause the liquid 14 to eject from the front end opening 12d of the nozzle portion 12c.

In the insertion device 10 shown in FIG. 1, an opening portion 20 is formed at a portion of the main body closer to the rear end than the hand-held portion 12e as an opening portion of the inner space of the main body 12 other than the front end opening 12d of the nozzle portion 12c. Specifically, a cylindrical member 22 having a screw portion for advancing the pushing shaft 16 in the pushing direction by screw action when inserting the lens 1 is inserted into the rear end of the main body 12 and the opening portion 20 is formed between the outer circumference of the cylindrical member 22 and the main body 12 as a gap- or groove-shaped path.

The opening portion 20 prevents a portion to be held by a hand between the lens holding portion 12b and the hand-held portion 12e from wetting because the liquid 14 in the main body 12 leaks from a gap of the configuration in which the lens holding portion 12b is vertically divided into two portions or a lid which can be opened or closed is used. That is, allowing extra liquid 14 to flow out from the opening portion 20 provided at a portion closer to the rear end than the hand-held portion 12e prevents the liquid 14 from leaking from the lens holding portion 12b. Thereby, the easiness for holding the insertion device 10 by a hand is not deteriorated.

The number, size and position of the opening portion for drainage are not restricted if the opening portion does not directly influence the flow of the liquid 14 to be supplied to the nozzle portion 12c. Moreover, it is allowed to connect a draining path having a small diameter to the flow path (hatched portion in FIG. 2) heading for the nozzle portion 12c from the introducing portion 24 such that the draining path does not influence the flow in the flow path.

A cylindrical intermediate member 25 extended up to a position close to the front end of the cylindrical portion 12a from the rear end of the main body 12 is pressed into the above-described cylindrical member 22. Then, an O-ring 23 for sealing is provided, in the inside of the intermediate member 25, at a portion of the first shaft portion 16a slightly closer to the rear end than the flow-out opening 16e. Therefore, the liquid 14 is prevented from leaking from the inside of the cylindrical member 22.

Thus, in the case where the flow-out opening 16e is provided to a position slightly closer to the nozzle portion 12c than the sealed portion by the O-ring 23, some of the liquid 14 flows to the opposite side to the nozzle portion 12c when the liquid flows into the main body 12 from the flow-out opening 16e. However, since the immediately rear portion thereof is sealed by the O-ring 23, the liquid 14 immediately flows toward the nozzle portion 12c.

Then, it is possible to restrain the flow of the liquid 14 to the vicinity of the opening portion 20 for drainage by this backflow preventive configuration and to minimize the liquid leak from the opening portion 20. That is, it is possible to prevent unnecessary liquid leak.

It should be noted that this embodiment uses a plurality of O-rings 23 because only one O-ring 23 cannot completely prevent the liquid leak. However, using the plurality of O-rings 23 increases the frictional resistance between the O-rings 23 and the intermediate member 25, thereby resulting in a difficulty for performing delicate and smooth operation of the pushing shaft 16. Therefore, it is recommended to slightly increase the diameter of one O-ring 23 by attaching importance to the liquid-leak cutoff function and slightly decrease diameters of other O-rings 23 so that outflow of leaked liquid can be avoided. That is, the use of the plurality of O-rings 23 having different sizes makes it possible to prevent the liquid leak and obtain appropriate operational feeling of the pushing shaft 16.

Figure 3A:
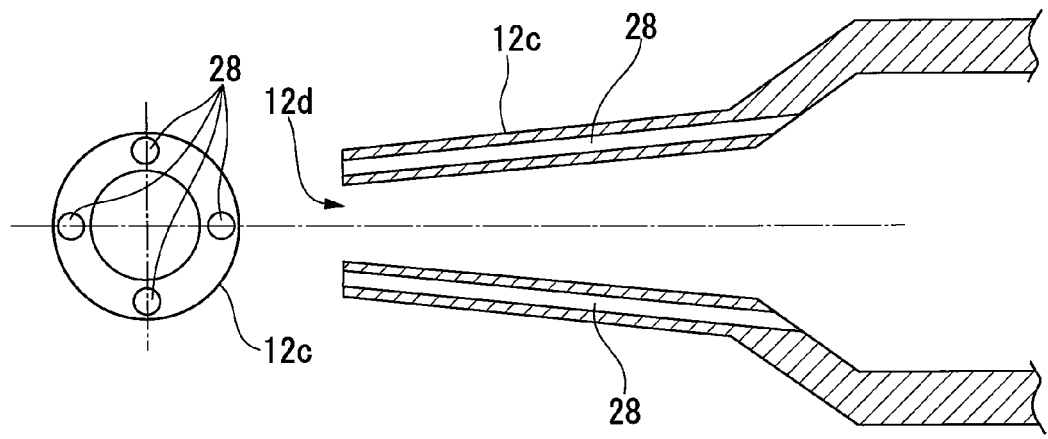
FIG. 3A is a sectional view showing a configuration of the nozzle portion of Embodiment 1.
Figure 3B:
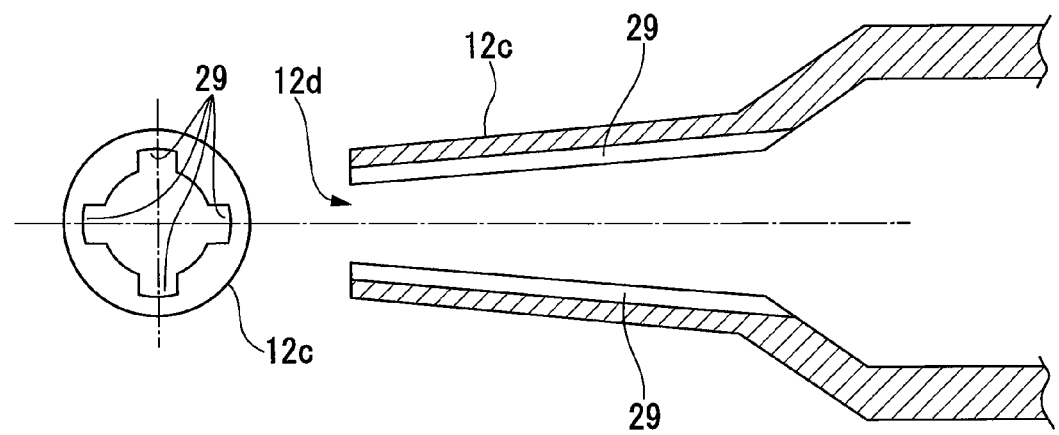
FIG. 3B is a sectional view showing the configuration of the nozzle portion of Embodiment 1.

FIGS. 3A and 3B show sectional shapes of the nozzle portion 12c. Illustrations at the right side of FIGS. 3A and 3B are cross sections obtained by cutting the nozzle portion 12c along the lens pushing direction and illustrations at the left side of FIGS. 3A and 3B are cross sections orthogonal to the lens pushing direction of the nozzle portion 12c.

When the lens 1 passes through the nozzle portion 12c, a space through which the liquid 14 passes in the nozzle portion 12c becomes very small because the lens 1 is present. Therefore, the flow rate of the liquid 14 ejected from the nozzle portion 12c decreases and the anterior chamber of the eye may not sufficiently swell.

Therefore, in this embodiment, as shown in FIGS. 3A and 3B, a hole (flow path) 28 or groove 29 for securing the area of the flow path of the liquid 14 is formed in the inside of the peripheral wall (that is, within the thickness of the peripheral wall) of the nozzle portion 12c or on the face (in inner peripheral face). The hole 28 and groove 29 open at the rear end of the nozzle portion 12c and extend in the longitudinal direction up to the front end opening 12d.

Figure 3C:
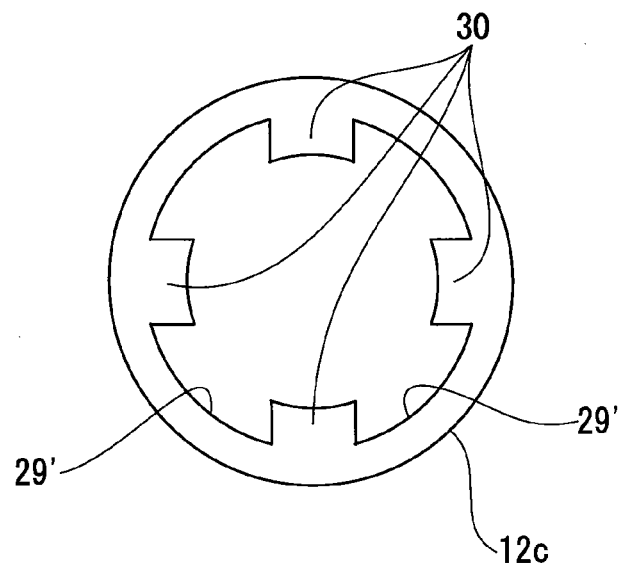
FIG. 3C is a sectional view showing the configuration of the nozzle portion of Embodiment 1.

Moreover, as shown in FIG. 3C, it is allowed to form a plurality of rails 30 extending in the longitudinal direction up to the front end opening 12d from the rear end of the nozzle portion 12c in the peripheral wall of the nozzle portion 12c. When the lens 1 moves in the nozzle portion 12c while contacting the rails 30, grooves 29' serving as flow paths for the liquid 14 are formed on the outer periphery of the lens 1.

According to these configurations, it is possible to sufficiently secure the flow rate of the liquid 14 to be supplied to the eye through the nozzle portion 12c from the main body 12 (cylindrical portion 12a) even if the lens 1 is present in the nozzle portion 12c. Therefore, it is possible to sufficiently swell the anterior chamber and smoothly insert the lens 1 thereinto.

Figure 3D:
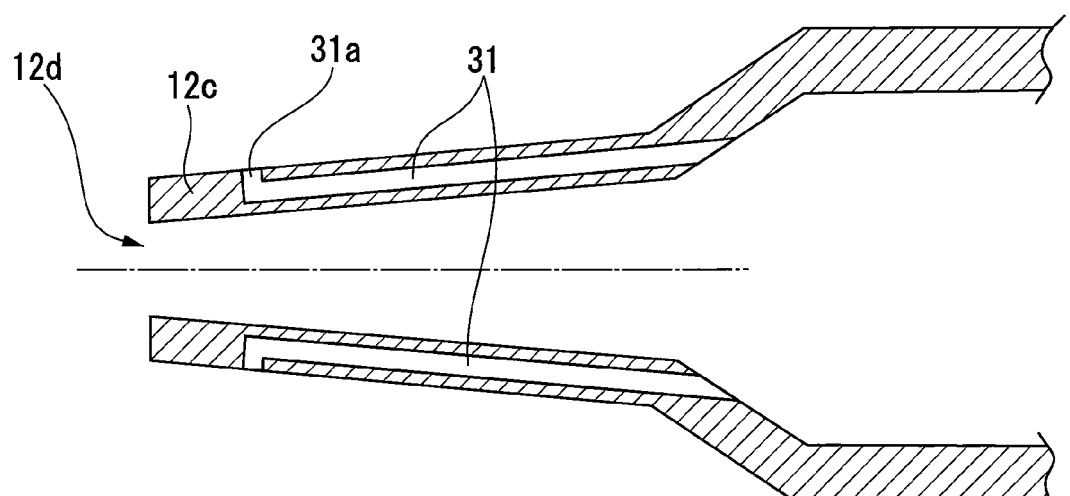
FIG. 3D is a sectional view showing the configuration of the nozzle portion of Embodiment 1.

Moreover, as shown in FIG. 3D, it is allowed that a hole (flow path) 31 extending in the longitudinal direction is formed in the peripheral wall of the nozzle portion 12c up to its front part to be inserted into the eye near the front end and the hole 31 is opened on the outer face of the peripheral wall of the front part of the nozzle portion 12c so that the liquid 14 is ejected.

By forming the hole 31 having the opening 31a on the outer face of the peripheral wall and inserting the nozzle portion 12c including the opening 31a into the anterior chamber when the anterior chamber of the eye is insufficiently swelled, it is possible to supply the liquid 14 into the anterior chamber to sufficiently swell it.

However, when the anterior chamber of the eye is sufficiently swelled, it is possible to avoid the liquid 14 from further entering the anterior chamber and the anterior chamber from excessively swelling (being excessively pressurized) by inserting only the front part of the nozzle portion 12c ahead of the opening 31a into the anterior chamber to expose the opening 31a outside the eye.

That is, by only adjusting the insertion amount of the nozzle portion 12c into the anterior chamber, it is possible to control the flow rate of the liquid 14 into the eye and optimize the pressure in the anterior chamber for lens insertion.

It is allowed to form the hole 31 shown in FIG. 3D and the hole 28 and grooves 29 and 29' shown in FIGS. 3A to 3C on the same nozzle portion 12c.

As described above, in this embodiment, the introducing portion 24 to be connected with the tube 13 is provided to the rear end of the pushing shaft 16. However, in a state in which the introducing portion 24 and tube 13 are exposed, it is difficult to insert and rotate the pushing shaft 16. Moreover, the tube 13 may be deformed by a hand for operating the pushing shaft 16 and supply of the liquid 14 to the insertion device 10 may be interrupted.

Therefore, in this embodiment, as shown in FIG. 1, the introducing portion 24 and a cover 32 for covering the vicinity of the end of the tube 13 connected with the introducing portion 24 are provided to the pushing shaft 16. Holding the cover 32 when operating the pushing shaft 16 makes it possible to easily operate the shaft 16 without deforming the tube 13.

Tubes used as the tube 13 to be connected with the introducing portion 24 have various diameters. For example, the size of the connector of the irrigation portion of an ultrasonic emulsification suction apparatus depends on the maker of the apparatus and the size of the tube 13 depends on the size of the connector. Moreover, if the flow rate of the liquid 14 can be adjusted by the size of the tube 13, this is convenient.

Figure 4:
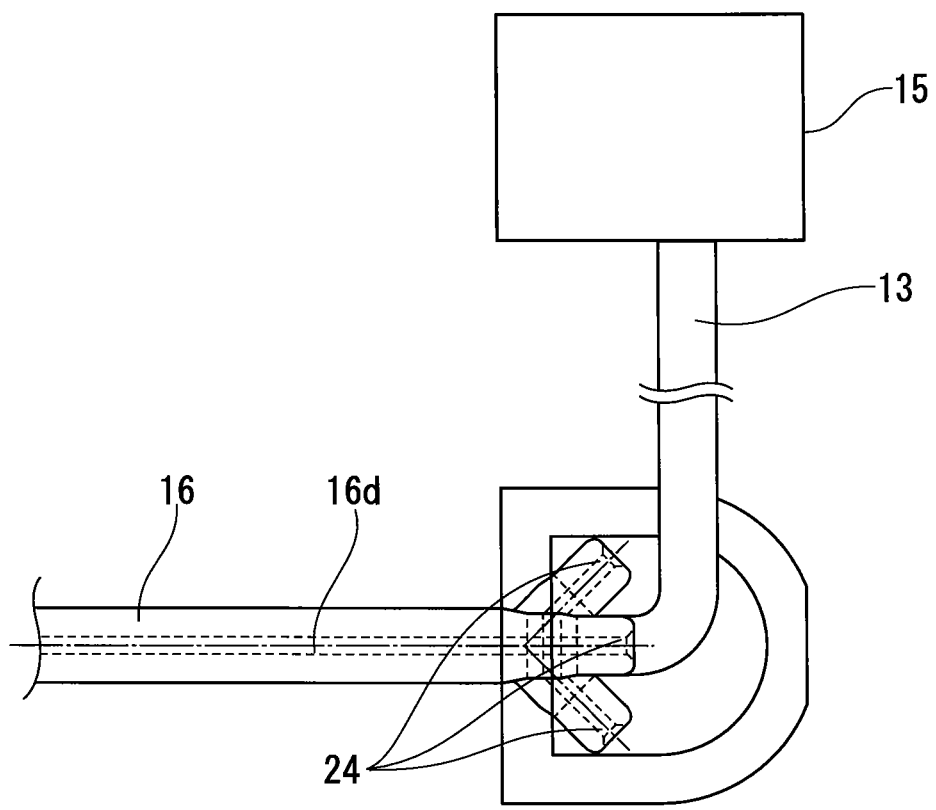
FIG. 4 is an illustration showing a modified example of the inserting system of Embodiment 1.

Therefore, as shown in FIG. 4, it is allowed to provide a plurality of introducing portions 24 having different sizes (sizes of connectable tubes 13) at the rear end of the pushing shaft 16. In this case, it is recommended that a plug or lid can be provided to the introducing portion 24 not connecting with the tube 13.

Moreover, since this system uses the liquid 14 such as normal saline having a low viscosity, the operation of the pushing shaft 16 becomes easy compared to the case of using a viscoelastic material, and thereby the pushing shaft 16 may be fast pushed. Increasing the diameter of the O-ring 23 can avoid this improper operation to a certain extent. However, this is not a complete solution.

Therefore, in this embodiment, a spring 35 is provided to the rear end of the main body 12 (outer periphery of the pushing shaft 16) as shown in FIG. 1. Thereby, resistance is provided for the inserting operation of the pushing shaft 16 and the improperly fast inserting operation can be avoided.

In this system capable of ejecting the lens 1 and the liquid 14 such as normal saline, use feeling is improved when the flow rate of the liquid 14 into the eye can be controlled. Because it is possible to correspond to various situations in the surgeries, for example, a situation in which an intraocular pressure should be set to a low value when inserting the lens 1.

Figure 5A:
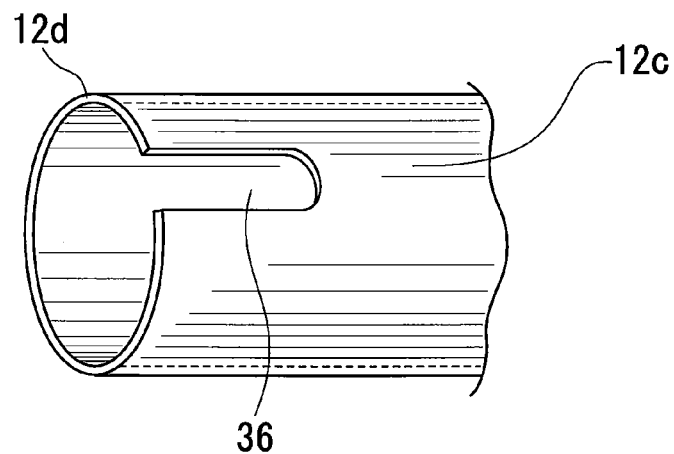
FIG. 5A is a perspective view showing the configuration of the nozzle portion of Embodiment 1.
Figure 5B:
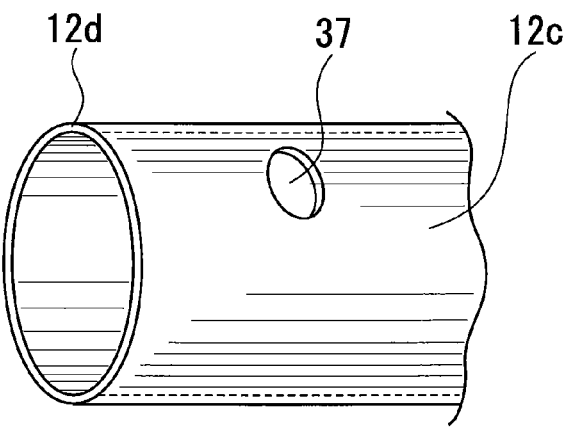
FIG. 5B is a perspective view showing the configuration of the nozzle portion of Embodiment 1.

Therefore, it is allowed to form the hole 31 as shown in FIG. 3D in the peripheral wall of the nozzle portion 12c. However, as shown in FIGS. 5A and 5B, it is allowed to form a slit 36 or nozzle hole 37 passing through the peripheral wall of the nozzle portion 12c in the diameter direction nearby the front end opening 12d of the nozzle portion 12c. The slit 36 is a groove-shaped opening connected to the front end opening 12d. Moreover, the nozzle hole 37 is a hole separately from the front end opening 12d.

Figure 5C:
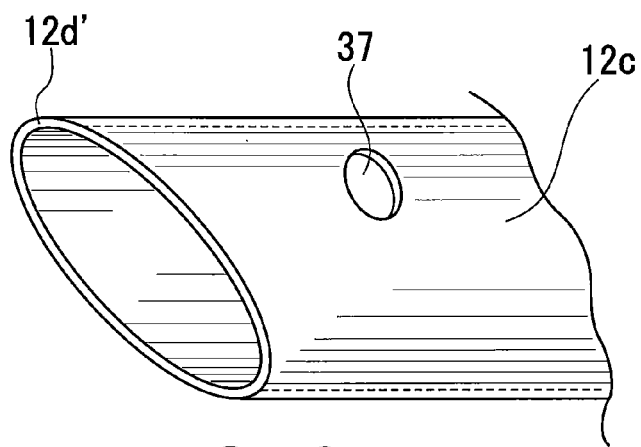
FIG. 5C is a perspective view showing the configuration of the nozzle portion of Embodiment 1.

Moreover, as shown in FIG. 5C, it is allowed to form the front end opening 12d' of the nozzle portion 12c so that the opening 12d' becomes oblique to the lens pushing direction.

When the swell of the anterior chamber is insufficient, the slit 36 and nozzle hole 37 are inserted into the anterior chamber together with the front end opening 12d or the whole of the oblique front end opening 12d' is inserted into the anterior chamber.

On the other hand, when the swell of the anterior chamber of the eye is sufficient, it is possible to eject some of the liquid 14 flown into the nozzle portion 12c to the outside of the eye by exposing at least a part of the slit 36, the nozzle hole 37 and the front end opening 12d' outside the anterior chamber. Thereby, it is possible to control the quantity of the liquid 14 which is flown into the eye from the front end openings 12d and 12d' of the nozzle portion 12c.

In addition, since it is not necessary that the liquid 14 always flows during a surgery, it is convenient if the flow of the liquid 14 can be stopped according to necessity. Therefore, in this embodiment, a clip 38 is provided to the tube 13 as shown in FIG. 1 so that it is possible to flow or stop the liquid 14 by setting or removing the clip 38 according to necessity. Thereby, the quantity of the liquid 14 to be used decreases and wetting of a surgery room due to ejection of unnecessary liquid 14 is prevented.

Embodiment 2

Figure 6:
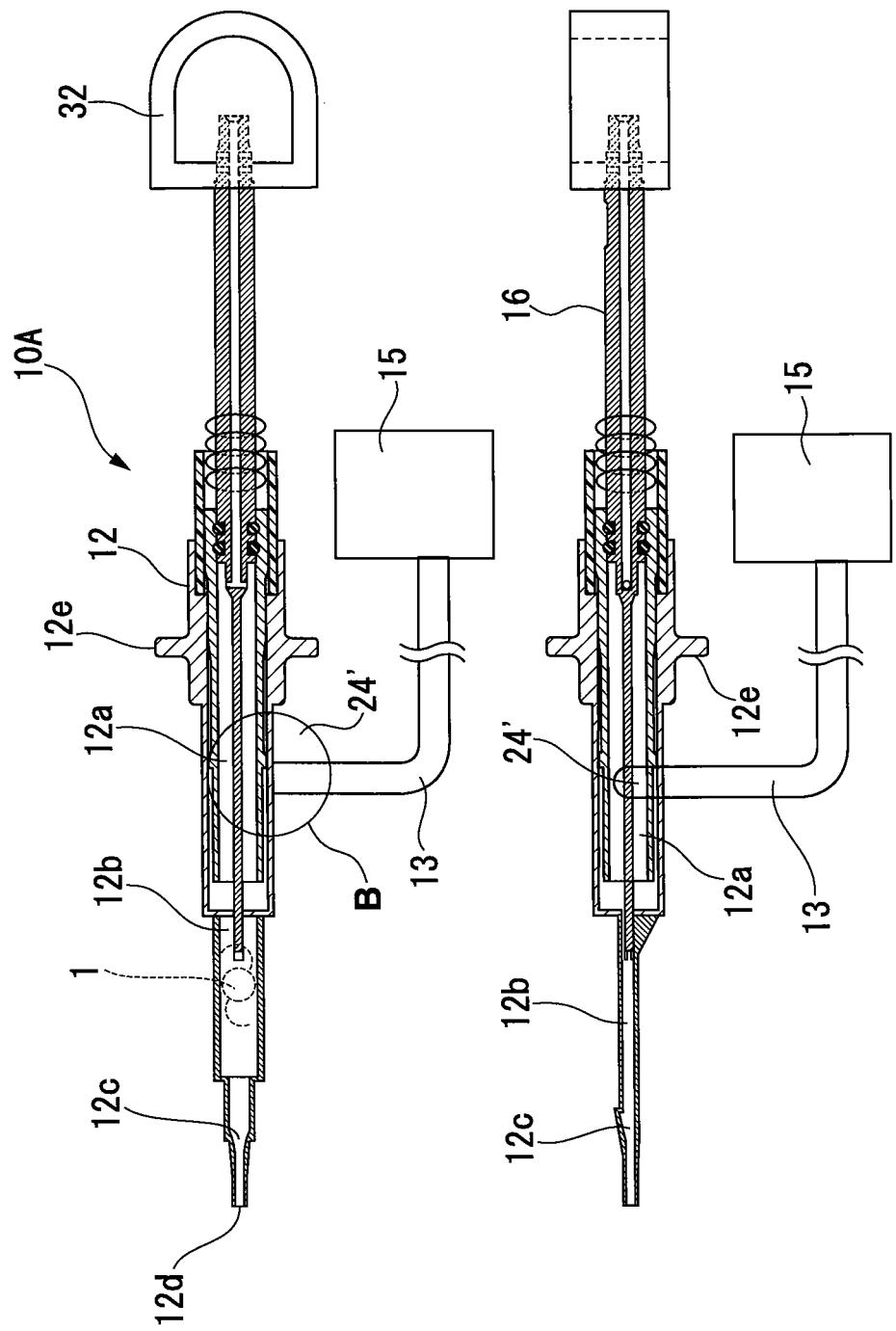
FIG. 6 is top view and side view showing an intraocular lens inserting system which is Embodiment 2 of the present invention.

FIG. 6 shows a top view and a side view of the insertion system which is Embodiment 2 of the present invention. In this embodiment, component elements or component portions common to Embodiment 1 are provided with the same symbols as those in Embodiment 1.

In the case of the insertion device 10A of this embodiment, liquid is supplied to an introducing portion 24' provided to a cylindrical portion 12a of a main body 12 from a feeder 15 through a tube 13. In this case, the flow path in the pushing shaft 16 described in Embodiment 1 is unnecessary. Therefore, the configuration becomes simple compared to the insertion device of Embodiment 1.

Embodiment 3

Figure 7:
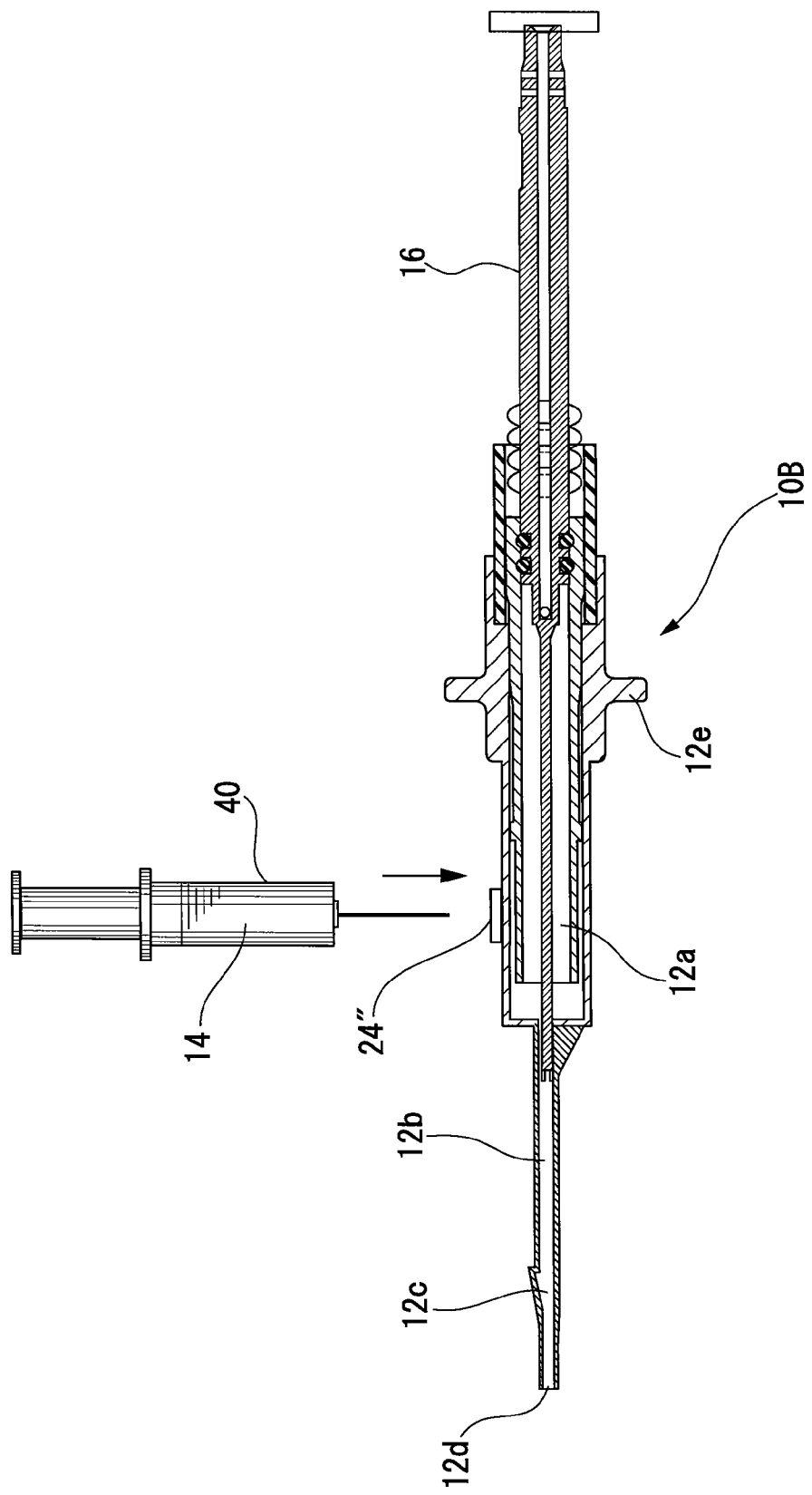
FIG. 7 is a side view showing an intraocular lens inserting system which is Embodiment 3 of the present invention.

FIG. 7 shows a side view of an insertion system which is Embodiment 3 of the present invention. In this embodiment, component elements or component portions common to Embodiments 1 and 2 are provided with the same symbol as those in Embodiments 1 and 2.

Also in the insertion device 10B of this embodiment, an introducing portion 24" is provided to a cylindrical portion 12a of a main body 12. In this embodiment, however, the needle of a syringe 40 is inserted into the introducing portion 24" to introduce the liquid 14 into the main body 12 from the syringe 40.

Also in this case, the flow path in the pushing shaft 16 described in Embodiment 1 is unnecessary. Therefore, the configuration becomes simple compared to the case of the insertion device of Embodiment 1. Moreover, since connection of a tube to the main body 12 is unnecessary, handling of the insertion device is easy.

Embodiment 4

Figure 8:
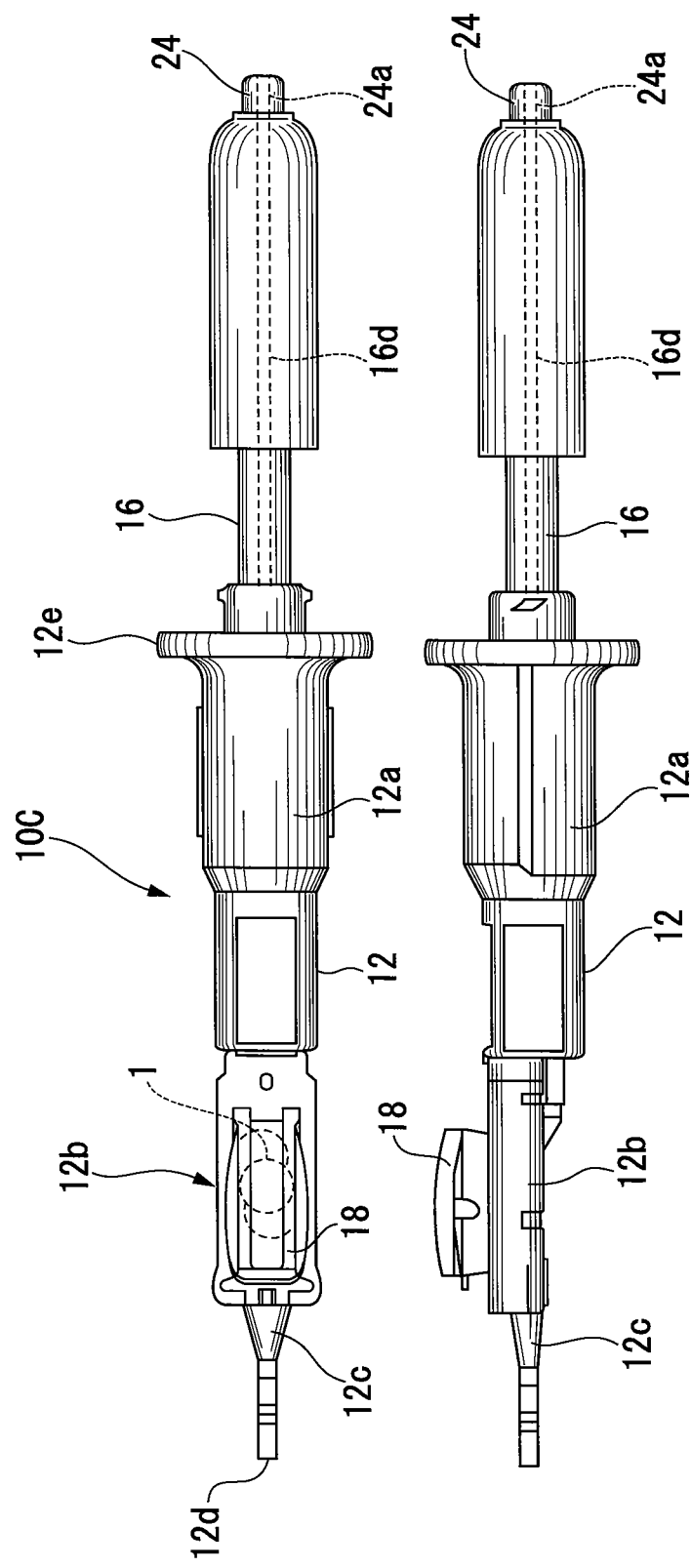
FIG. 8 is top view and side view of an intraocular lens inserting system of Embodiment 4 of the present invention.

FIG. 8 shows a top view and a side view of the insertion device 10C which is Embodiment 4 of the present invention. The insertion device 10C is constituted of a cylindrical portion 12a, a lens holding portion 12b, a main body 12 having a hand-held portion 12e, and a nozzle 12c attached to the front end of the lens holding portion 12b.

A deformation mechanism 18 is provided to the lens holding portion 12b, which moves the lens 1 into the inside lower space of the lens holding portion 12b while deforming the lens 1 from a state of holding the lens 1 without substantially applying a stress. The movement of the lens 1 down to the space enables the insertion of the lens 1 into the eye by the pushing shaft 16.

An introducing portion 24 and a flow path 16d are formed on/in the pushing shaft 16 of this insertion device 10C similarly to the insertion device 10 in FIG. 1 and a flow-out opening, not shown, is formed on the intermediate portion of the pushing shaft 16.

In the insertion device 10C of this embodiment, it is allowed to form an introducing portion on the cylindrical portion 12a and introduce liquid thereinto by connecting a tube or inserting the needle of a syringe similarly to the insertion devices of Embodiments 2 and 3.

Moreover, in the insertion devices 10A to 10C shown in this embodiment and Embodiments 2 and 3, a hole, a groove, or an opening serving as the flow path or the ejecting opening for the liquid 14 may be formed on the peripheral wall of the nozzle (portion) 12c as shown in FIGS. 3A to 3D and FIGS. 5A to 5C.

Moreover, configurations shown in FIGS. 3A to 3D and 5A to 5C can be applied to insertion devices having no introducing portion on the main body. For example, the configuration can be applied to an insertion device in which liquid is introduced into the main body by inserting the front end opening of a nozzle into liquid in a vessel such as a beaker and pulling an pushing shaft in the direction opposite to the lens inserting direction.

Thus, the present invention can be applied to insertion devices of various configurations. Liquid used for the present invention is not limited to normal saline.

According to the above-described Embodiments 1 and 4, it is possible to supply the liquid such as normal saline into the main body through the introducing portion provided to the pushing shaft or the main body. The liquid supplied into the main body flows through a space (including the inside of nozzle) in which the lens moves and is ejected from the front end of the nozzle. Therefore, even if a viscoelastic material is not used, it is possible to execute a lubricating function for the lens in the main body and a function of swelling the space of the anterior chamber of the eye by properly setting the flow rate of the liquid.

Moreover, by using liquid such as normal saline having a low viscosity, the lens inserting space in the eye is not blocked and it is possible to smoothly insert the lens into the eye.

Furthermore, the flow path for the liquid formed within the thickness of the peripheral wall of the nozzle or the groove formed on the inner face of the peripheral wall of the nozzle makes it possible to sufficiently secure the flow rate of the liquid into the eye or to the outside of the eye even if the lens is present in the nozzle.

Furthermore, the ejecting opening for the liquid provided to the peripheral wall of the nozzle makes it possible to control the inflow amount of the liquid into the eye by only adjusting the inserting distance of the nozzle into the eye.

Furthermore, the present invention is not limited to these preferred embodiments and various variations and modifications may be made without departing from the scope of the present invention.

This application claims foreign priority benefits based on Japanese Patent Applications Nos. 2005-367171, filed on Dec. 20, 2005, and 2006-205397, filed on Jul. 27, 2006, and each of which is hereby incorporated by reference herein.

What is claimed is:

1. An insertion device for inserting a lens into an eye, comprising:
  a main body having a nozzle at its front end; and
  a pushing member for pushing the lens set in the main body into the eye through a front end opening of the nozzle,
  wherein the insertion device further comprises:
    an introducing opening through which liquid for lubricating the lens in the main body and for swelling a space of an anterior chamber of the eye is introduced into the main body, the introducing opening being provided separately from the front end opening of the nozzle; and
    an ejecting opening through which liquid is ejected from an inside of the main body to an outside of the main body, the ejecting opening disposed in a side wall of the nozzle separately from both the introducing opening and the front end opening of the nozzle to flow extra liquid there through to prevent the liquid from leaking from the main body, the ejecting opening disposed in the side wall of the nozzle such that, when the nozzle is inserted into an eye, the liquid may flow through the ejecting opening into the eye when the nozzle is in a first position within the eye, and wherein the liquid may flow through the ejecting opening outside the eye while the front end opening of the nozzle remains in the eye when the nozzle is in a second position within the eye.

2. The insertion device according to claim 1, wherein the introducing opening is provided to the rear end of the pushing member.

3. The insertion device according to claim 1, wherein the pushing member includes a lens contact portion for contacting the lens at its front end, and a flow-out opening for supplying the liquid from a flow path into the inner space of the main body is provided at a position closer to the rear end than the lens contact portion of the pushing member.

4. The insertion device according to claim 1, wherein a plurality of the introducing openings are provided to the pushing member.

5. The insertion device according to claim 1, further comprising a cover which is attached to the pushing member and covers the introducing opening and the end of a tube connected to the introducing opening for supplying the liquid.

6. A lens-containing insertion device, comprising:
  a lens;
  a main body having a lens holding portion and a nozzle; and
  a pushing member for pushing the lens held in the lens holding portion into an eye through a front end opening of the nozzle,
  wherein the insertion device further comprises:
    an introducing opening through which liquid for lubricating the lens in the main body and for swelling a space of an anterior chamber of the eye is introduced into the main body, the introducing opening being provided separately from the front end opening of the nozzle; and
    an ejecting opening through which liquid is ejected from an inside of the main body to an outside of the main body, the ejecting opening disposed in a side wall of the nozzle separately from both the introducing opening and the front end opening of the nozzle to flow extra liquid there through to prevent the liquid from leaking from the lens holding portion, the ejecting opening disposed in the side wall of the nozzle such that, when the nozzle is inserted into an eye, the liquid may flow through the ejecting opening into the eye when the nozzle is in a first position within the eye, and wherein the liquid may flow through the ejecting opening outside the eye while the front end opening of the nozzle remains in the eye when the nozzle is in a second position within the eye.

7. The insertion device according to claim 6, wherein the introducing opening is provided to the rear end of the pushing member.

8. The insertion device according to claim 6, wherein the pushing member includes a lens contact portion for contacting the lens at its front end, and a flow-out opening for supplying the liquid from a flow path into the inner space of the main body is provided at a position closer to the rear end than the lens contact portion of the pushing member.

9. The insertion device according to claim 6, wherein a plurality of the introducing openings are provided to the pushing member.

10. The insertion device according to claim 6, further comprising a cover which is attached to the pushing member and covers the introducing opening and the end of a tube connected to the introducing opening for supplying the liquid.

* * * * *